US007875058B2

(12) United States Patent
Holmes, Jr.

(10) Patent No.: US 7,875,058 B2
(45) Date of Patent: Jan. 25, 2011

(54) BUNION REPAIR USING SUTURE-BUTTON CONSTRUCT

(75) Inventor: George B. Holmes, Jr., Naperville, IL (US)

(73) Assignee: Arthrex, Inc., Naples, FL (US)

( * ) Notice: Subject to any disclaimer, the term of this patent is extended or adjusted under 35 U.S.C. 154(b) by 540 days.

(21) Appl. No.: 12/016,129

(22) Filed: Jan. 17, 2008

(65) Prior Publication Data
US 2008/0208252 A1 Aug. 28, 2008

Related U.S. Application Data

(60) Provisional application No. 60/880,723, filed on Jan. 17, 2007.

(51) Int. Cl.
A61B 17/04 (2006.01)
A61B 17/84 (2006.01)
A61F 2/08 (2006.01)

(52) U.S. Cl. ........................ 606/232; 606/300
(58) Field of Classification Search .............. 623/21.19, 623/908; 128/898; 606/232, 300, 86 R, 606/96, 60, 254, 255, 260, 263
See application file for complete search history.

(56) References Cited

U.S. PATENT DOCUMENTS

| 4,159,716 | A | * | 7/1979 | Borchers | 606/96 |
| 4,409,974 | A | * | 10/1983 | Freedland | 606/60 |
| 5,306,301 | A | * | 4/1994 | Graf et al. | 606/232 |
| 5,529,075 | A | * | 6/1996 | Clark | 128/898 |
| 5,888,203 | A | * | 3/1999 | Goldberg | 623/13.11 |
| 6,391,031 | B1 | * | 5/2002 | Toomey | 606/87 |
| 6,719,801 | B1 | * | 4/2004 | Holt | 623/21.11 |
| 6,964,645 | B1 | * | 11/2005 | Smits | 602/30 |
| 7,235,091 | B2 | * | 6/2007 | Thornes | 606/232 |
| 2003/0023268 | A1 | * | 1/2003 | Lizardi | 606/232 |
| 2003/0236555 | A1 | * | 12/2003 | Thornes | 606/232 |
| 2006/0178702 | A1 | * | 8/2006 | Pierce et al. | 606/232 |
| 2006/0264961 | A1 | * | 11/2006 | Murray-Brown | 606/88 |
| 2007/0010818 | A1 | * | 1/2007 | Stone et al. | 606/72 |

(Continued)

FOREIGN PATENT DOCUMENTS

WO   WO 2009/018527   *   2/2009

OTHER PUBLICATIONS

Huber et al., The Mitek Mini Anchor in teh Treatment of Gamekeeper's Thumb, 1997, Eurepean Journal of Plastic Surgery, 20: 251-255.*

(Continued)

*Primary Examiner*—Darwin P Erezo
*Assistant Examiner*—Dianne Dornbusch
(74) *Attorney, Agent, or Firm*—Dickstein Shapiro LLP

(57) ABSTRACT

A method for bunion repair using a suture-button construct. The suture-button construct includes a first button, a second button, a first suture strand, a pull-through suture strand and a needle. The first and second buttons have apertures to facilitate the suture strands to pass through the buttons. The first suture strand is double looped through the first and second buttons and the pull-through suture strand is looped through one of the apertures of the first button. The pull-through suture strand also loops through an eyelet of the needle and thus, is operatively associated with the needle. A suture anchor-button construct can also be used for bunion repair.

6 Claims, 17 Drawing Sheets

U.S. PATENT DOCUMENTS

| | | | |
|---|---|---|---|
| 2008/0177302 A1* | 7/2008 | Shurnas | 606/228 |
| 2008/0269743 A1* | 10/2008 | McNamara et al. | 606/60 |
| 2008/0281355 A1* | 11/2008 | Mayer et al. | 606/228 |
| 2009/0036893 A1* | 2/2009 | Kartalian et al. | 606/60 |
| 2010/0076504 A1* | 3/2010 | McNamara et al. | 606/86 R |
| 2010/0152752 A1* | 6/2010 | Denove et al. | 606/148 |
| 2010/0211071 A1* | 8/2010 | Lettmann et al. | 606/60 |
| 2010/0268273 A1* | 10/2010 | Albertorio et al. | 606/232 |

OTHER PUBLICATIONS

James W. Miller, M.D. Distal First Metatarsal Displacement Osteotomy: Its Place in the Schema of Bunion Surgery, 1975, the Journal fo Bone and Joint Surgery, 56:923-931.*

H. Kelikiam, M.D., Hallux Valgus, Allied Deformities of the Forefoot and Metatarsalgia, 1965, W.B. Saunders Company, pp. 253-256.*

* cited by examiner

BUNION REPAIR USING SUTURE-BUTTON CONSTRUCT

CROSS REFERENCE TO RELATED APPLICATIONS

This application claims priority to U.S. Provisional Application No. 60/880,723, filed on Jan. 17, 2007, the entire disclosure of which is hereby incorporated by reference.

BACKGROUND OF THE INVENTION

1. Field of the Invention

The present invention relates to the field of surgery and, in particular, to a bunion repair technique using a suture-button construct and a device.

2. Description of the Related Art

"Bunion" refers to the pathological bump or inflammation on the side of the great toe joint associated with either a bursal sac or a bony deformity involving the first metatarsal bone, the bone to which the great toe attaches.

Bunions are also associated with two other conditions: a deviated position of the great toe where the great toe leans in towards the second toe, and a deviation in the angle between the first and second metatarsal bones of the foot. As the first metatarsal bone drifts away from its normal position, the small bones, termed "sesamoids," found beneath the first metatarsal may also become deviated over time.

In some cases, bunion may be so severe that the great toe begins to slant towards the outside of the foot, a condition called "hallux valgus."

"Hallux valgus" or "hallux abducto valgus" is associated with bunion deformity, where "hallux" refers to the great toe, "valgus" refers to the abnormal slant of the great toe, and "abducto" refers to the abnormal slant or inward leaning of the great toe towards the second toe.

The abnormalities associated with bunion development are caused by a biomechanical abnormality, where certain tendons, ligaments, and supportive structures of the first metatarsal are no longer functioning correctly. This biomechanical abnormality may be due to the structure of the foot—flat feet, excessive ligamentous flexibility, abnormal bone structure—or certain neurological conditions.

The treatment of hallux valgus deformity includes an assessment of the hallux valgus angle, the intermetatarsal angle and the contribution of an interphalageus deformity. Additionally, the presence or absence of arthritic involvement of both the first metatarsocuneiform joint and the first metatarsophalangeal joint are also assessed. The orientation of the distal metatarsal articular angle and the orientation of the first metatarsocuneiform joint are also considered.

A bunion repair is a surgical procedure performed on the great toe joint. The purpose is to correct a deformity of the great toe or to remove a painful bunion at its base.

Bunions may be treated by surgery. For instance, surgical procedures may address some combination of removing the abnormal bony enlargement of the first metatarsal, realigning the first metatarsal relative to the adjacent metatarsal, straightening the great toe relative to the first metatarsal and adjacent toes, realigning the cartilagenous surfaces of the great toe joint, repositioning the sesamoid bones beneath the first metatarsal, and correcting any abnormal bowing or misalignment within the great toe.

Various methods to correct the intermetatarsal angle are known. Soft tissue correction can be achieved by suturing the lateral capsule of the first metatarsal to the medial capsule of the second metatarsal, incorporating the intervening, previously released adductor tendon. A loss of reduction can occur due to the forces that oppose the suture repair as well as the possibility that poor tissue quality can contribute to a loss of reduction.

When more rigid deformities of the intermetatarsal angle are present, it is generally reduced by using a distal or proximal osteotomy of the first metatarsal. Typically, a surgeon cuts into the foot near the bunion, and removes the excess growth of bone with a bone saw. Depending on the degree of deformity, the surgeon may need to cut into the bone of the great toe and realign the bones so that the great toe no longer slants to the outside. Improving the angle of the great toe and repairing the metatarsal bones may require a fastening means to hold them in place. The incisions are later closed with stitches, and a bandage is applied.

Such osteotomies can be technically challenging and difficult to perform. Further, the consequences and potential complications from such surgical procedures is a daunting list that includes delayed union, malunion, nonunion, excessive shortening of the first metatarsal, avascular necrosis, hardware failure and prolonged protected ambulation.

Thus, there is a need for a bunion repair technique that is simple, flexible and is performed by a minimally invasive lateral approach, with indirect placement of buttons across the first and second metatarsal.

SUMMARY OF THE INVENTION

The present invention overcomes the disadvantages of the prior art and fulfills the needs noted above by providing a surgical procedure for bunion repair using a suture-button construct with surgically useful qualities, including indirect placement of buttons and a minimally invasive approach.

The surgical procedure of the present invention may be performed under local anesthesia, i.e., an injection of Liodocaine, Marcaine or Dexamethoasone. The procedure involves making an incision into the skin and carefully working down to the great toe joint and bone. An osteotomy, cutting of the bone, may be performed utilizing a small cannulated cutter which allows for a very small incision to be made. The bony prominence may also be removed using a bone saw. The soft tissue structures around the joint are then modified. The bones in the great toe and the bone just behind it, called the first metatarsal, are then cut with a bone saw and corrections are made to them. These corrections are kept in place with a first and a second button held together by a suture-button construct extending across the first and second metatarsal.

The present invention includes a suture-button construct for use in bunion repair formed of a pair of buttons connected by suture strand. The first button has two apertures while the second button has four apertures, the apertures to allow the passage of suture strand. A first suture strand is fed through the first aperture of the second button and through, in turn, the second and first apertures of the first button and through the second and fourth apertures of the second button and through, in turn, the second and first apertures of the first button and through the third aperture of the second button. A second suture strand looped through one of the first and second apertures of the first button and is operatively associated with a needle. Preferably, the first suture strand is double looped through the first and second buttons. The buttons may be formed, for example, of titanium, stainless steel, PolyEtherEther-Ketone (PEEK) or Poly-L Lactic Acid (PLLA). The suture strand may be FiberWire® suture strand, sold by Arthrex, Inc. of Naples, Fla.

The present invention also includes a surgical method for repairing bunions using a suture-button construct. The method includes providing a suture-button construct as described above. A longitudinal incision over the medial aspect of the first metatarsophalangeal joint is made to expose the entire medial eminence. Inserting a cannulated guide wire, a guide hole is formed just proximal to the excised medial eminence at a slight plantar-to-dorsal angle to ensure accurate pin placement and penetration of the second metatarsal at its midpoint. Using a cannulated drill bit, a hole is drilled across the first metatarsal and through the second metatarsal for the placement of the suture-button construct. Alternatively, a K-wire (Kirschner wire) may be used to drill the hole.

A pull-through needle with a pull-through suture strand is passed through the hole at an angle lateral of the second metatarsal to a medial of the first metatarsal and stopped before a first button enters the hole. The pull-through suture strand is pulled and a lateral tension is simultaneously applied on a first suture strand such that the first button of the construct lies sideways for passage through the hole. The pull-through suture is now advanced while the pull-through needle is pulled medially. The first button of the construct is then advanced through the hole until it exits the hole through the first metatarsal on the medial side of the first metatarsal cortex. Upon exiting the hole, the first button is flipped and a lateral tension is applied on the first suture strand to seat the first button against the first metatarsal. The pull-through suture is then cut and removed the first button is anchored.

Subsequently, the free ends of the first suture strand are pulled to advance the second button of the construct to seat the second button against the second metatarsal. The free ends of the first suture strand are tied by making a surgeon's knot and two reverse half-hitches. Any remaining first suture strand is removed by cutting and pulling them out of the first and second buttons of the construct.

The surgical method can also optionally be performed in the opposite direction as that described above, such that the first button ends up on the lateral side of the second metatarsal.

The surgical method for repairing bunions using a suture-button construct, as described in the earlier paragraph, may also be performed by inserting the cannulated guide wire by starting between about 2.5 cm and about 3.5 cm distal to metatarsal-cuneiform joint on the first metatarsal just below midline, drilling a hole using a cannulated drill bit into the superior second metatarsal metaphyseal bone, observing under the C-arm, allowing the plantarflexion of the third metatarsal to allow passage of the guide pin, tightening the first button over the second metatarsal and the second button over the first metatarsal by pulling on the first suture strand, and securing the first suture strand by a knot.

One of the buttons used in the present invention has an oblong body with first and second apertures, each of the apertures being tapered and terminating in a respective apex, the respective apexes being directed away from each other and being located substantially about a longitudinal mid-line of the oblong body. Preferably, each aperture is substantially triangular in plan view. More preferably, each of the apertures has first, second and third sides and the first sides of the respective first and second apertures are substantially parallel. More preferably, the second and third sides of each aperture are of substantially the same length while being longer than the first side.

The first and second apertures of the oblong button can have any shape, provided that each aperture is tapered and terminates in a respective apex. In one preferred embodiment, the aperture is substantially triangular in plan view. In another embodiment, the aperture is an egg-shaped or oval aperture, the curved narrower end comprising the apex.

The suture-button construct of the present invention also includes a button with a round body having four apertures, each of the apertures being located substantially equidistant from the center of the round body. Preferably, each aperture is substantially round in plan view.

The round button may have any suitable dimension (diameter and thickness). For example, the round button may have a diameter of about 5.5 mm and a thickness of about 1.27 mm. The centers of the four apertures are about 1.27 mm from the center of the button and the centers of a first pair of apertures lie substantially along an axis passing through the center of the button. The axis connecting the centers of the remaining two apertures, i.e., a second pair of apertures, is substantially perpendicular to the axis connecting the centers of the first pair of apertures.

The apertures of the round button can have any shape, provided that each aperture is equidistant from the center of the round body. One preferred embodiment is an aperture, which is substantially round in plan view. Another embodiment is an egg-shaped or oval aperture. The round button can be a cup-shaped button in cross-section.

The suture-button construct and the surgical technique of the present invention have several advantages over other existing apparatuses and surgical procedures: (1) typically, patients who undergo bunion repair in accordance with the present invention are required to wear post-operation shoe or boot for about 4-5 weeks in comparison to about 8-12 weeks for patients who undergo other bunion repair procedures; (2) post-operation morbidity for patients is significantly reduced; and (3) the suture-button construct provides great strength and security in comparison to a soft tissue repair.

These and other features and advantages of the present invention will become apparent from the following description of the invention that is provided in connection with the accompanying drawings and illustrated embodiments of the invention.

DETAILED DESCRIPTION OF THE PREFERRED EMBODIMENTS

The present invention is method and apparatus for bunion repair, which utilizes a suture-button construct that is placed across the first and second metatarsal.

Figure 1:
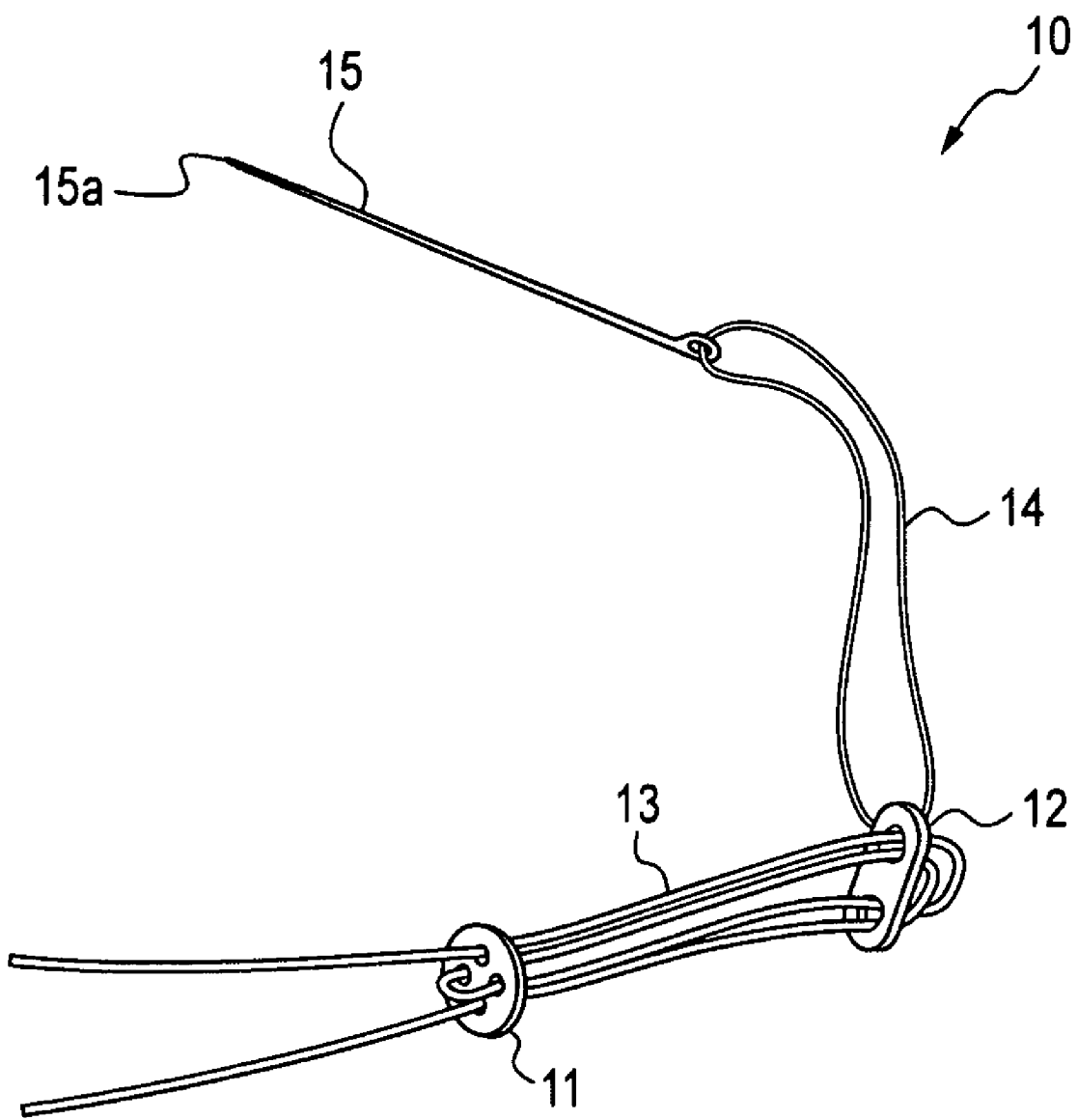
FIG. 1 illustrates a perspective view of assembled suture-button construct of the present invention.
Figure 2C:
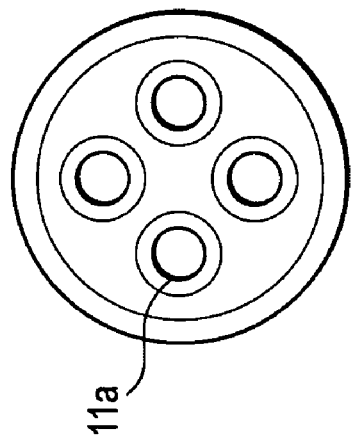
FIG. 2 illustrates a front, side, perspective view of a round button which forms part of the suture-button construct of the present invention.
Figure 2B:
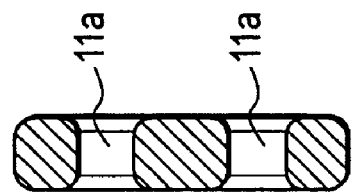
Figure 2A:
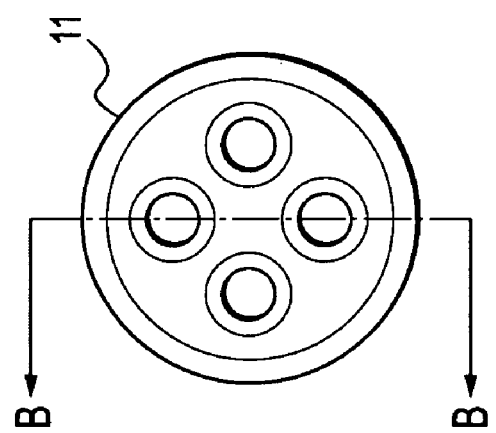
Figure 3B:
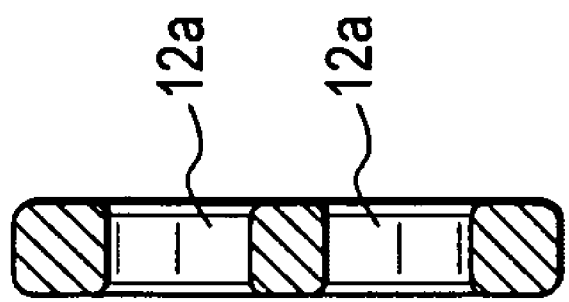
FIG. 3 illustrates a front, side, perspective view of an oblong button which forms part of the suture-button construct of the present invention.
Figure 3A:
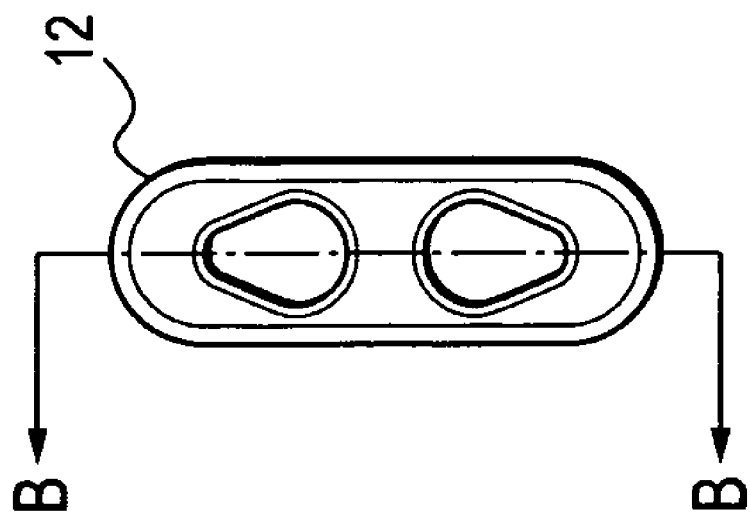

Referring to FIG. 1, the suture-button construct 10 of the present invention is formed of a first button 12, a second button 11, a first suture strand 13 double looped through the apertures 11a (FIG. 2), 12a (FIG. 3) of the first button 11 and the second button 12. The suture-button construct 10 also includes a pull-through needle 15 with a pull-through suture strand 14 looped through an aperture 12a (FIG. 3) of the first button 12. The first button 12 is preferably oblong in shape (FIG. 3). The second button 11 is preferably round in shape (FIG. 2).

TABLE 1

Apparatus of the present invention

| First Button | |
|---|---|
| Overall dimensions: | 8.0 mm (length) × 2.6 mm (width) × 1.3 mm (thickness) |
| Basic shape: | Oblong in plan shape, with chamfered or rounded corners and edges - this reduces the chance of the button being palpated under the skin and in addition, eases the passage of the first button through the hole as will be explained hereinafter |
| Button material: | Titanium, stainless steel, PEEK or PLLA |
| Button apertures: | 2 apertures (triangular in plan shape) |
| Aperture dimensions: | 2 mm base × 2 mm perpendicular height (equilateral triangle with chamfered corners), 1 mm distance between first and second apertures |
| Second Button | |
| Overall dimensions: | 5.5 mm (diameter) × 1.27 mm (thickness) |
| Basic shape: | Round in plan shape, with chamfered or rounded corners and edges |
| Button material: | Titanium, stainless steel, PEEK or PLLA |
| Button apertures: | 4 apertures (circular in plan shape), centers of the apertures at about 1.27 mm from the center of the button |
| Aperture dimensions: | 0.95 mm (diameter) (free of burrs or sharp edges) |
| First suture strand | |
| Suture material: | #2 FiberWire ®, blue in color (FiberWire ® is made of ultra-high molecular weight polyethylene (UHMWPE) and polyester, braided over a UHMWPE core) |
| Suture use: | Looped twice through the first and second apertures of the first and second buttons, leaving the two free ends of suture strand free for tying |
| Pull-through needle | 127 mm long straight needle with pull-through suture strand attached |
| Pull-through suture strand | |
| Suture material: | #2 FiberWire ®, white in color (FiberWire ® is made of ultra-high molecular weight polyethylene (UHMWPE) and polyester, braided over a UHMWPE core) |
| Suture use: | Looped once through an aperture of the first button, both free ends of pull-through suture strand being attached through the eye of the pull-through needle |
| Guidewire | 1.2 mm (diameter) |
| Cannulated Drill Bit | Stainless steel (material), 178 mm (length) × 2.7 mm (diameter), 1.35 mm cannulation for a guidewire to pass through |

The first suture strand 13 used in the present invention may be of any material, which is suitable for this purpose, whether absorbable or non-absorbable, provided it is sufficiently strong. A #2 FiberWire® suture strand, blue in color, is preferred. The #2 FiberWire® is a braided suture strand with an ultrahigh molecular weight polyethylene core and has almost twice the strength of a similarly sized generic suture strand. The #2 FiberWire® suture strand is a non-absorbable suture strand with increased abrasion-resistance, which knots easily without slipping.

The pull-through suture strand 14 used in the apparatus of the present invention may be formed of any suitable material, whether absorbable or non-absorbable, provided it is sufficiently strong. A #2 FiberWire® suture strand, white in color, is preferred.

The pull-through needle 15 may be of any dimensions, provided it is long enough to span the foot. The tip 15a of the pull-through needle 15 can be either "taper cut" or "cutting."

Figure 4:
FIG. 4 illustrates a plan view of a cannulated drill bit used in the present invention.

Referring to FIG. 4, a cannulated drill bit 16, preferably a 2.7 mm drill bit, is used to drill a hole for the first suture strand 13 and the pull-through suture strand 14. Alternatively, a K-wire (Kirschner wire) may be used to drill the hole. The diameter of the hole must be sufficient to permit the first button 12 to be pulled, lengthways, thereto.

Surgical Technique

Figure 5A:
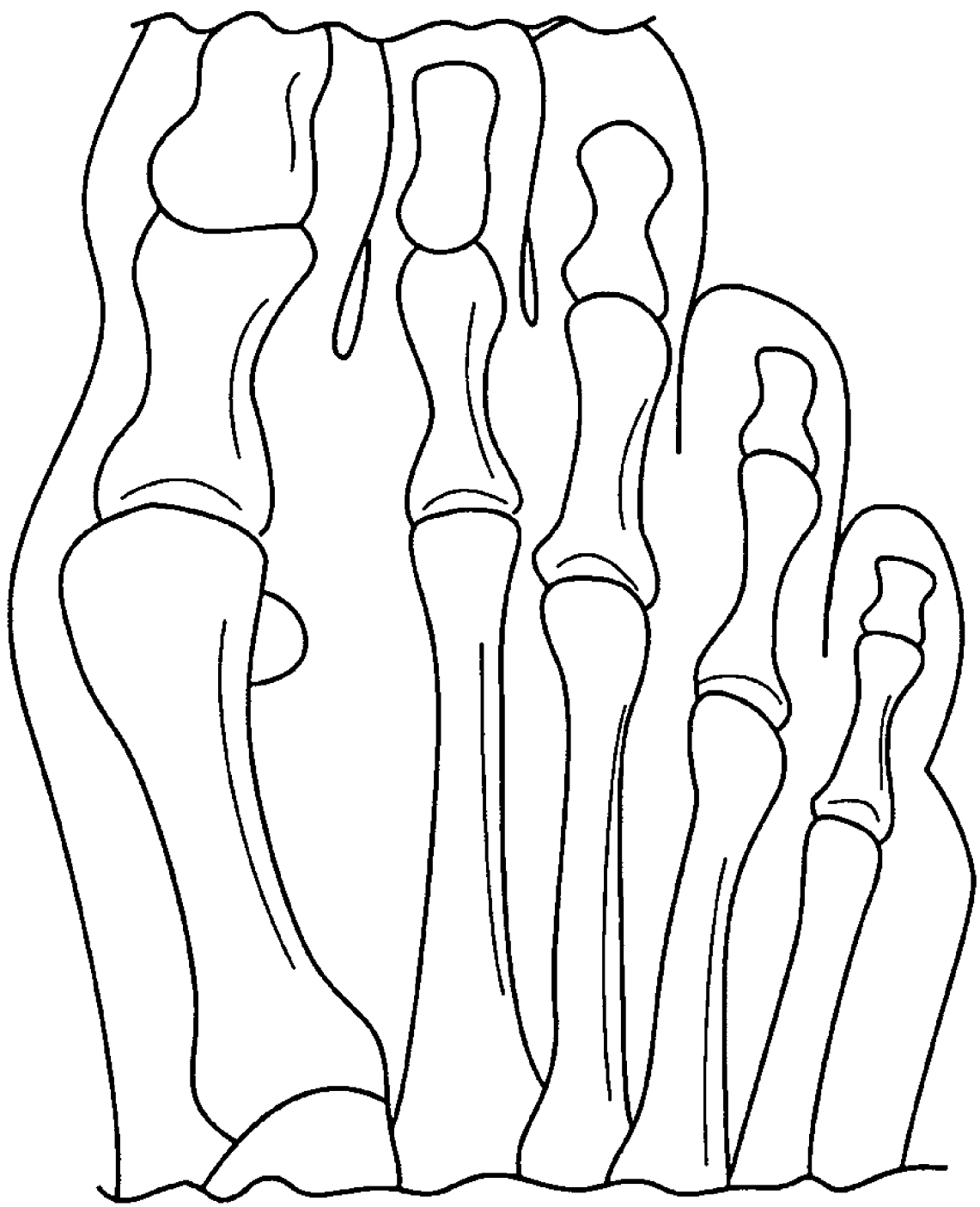
FIG. 5A shows a patient's foot with hallux valgus prior to performing a bunion repair.
Figure 5B:
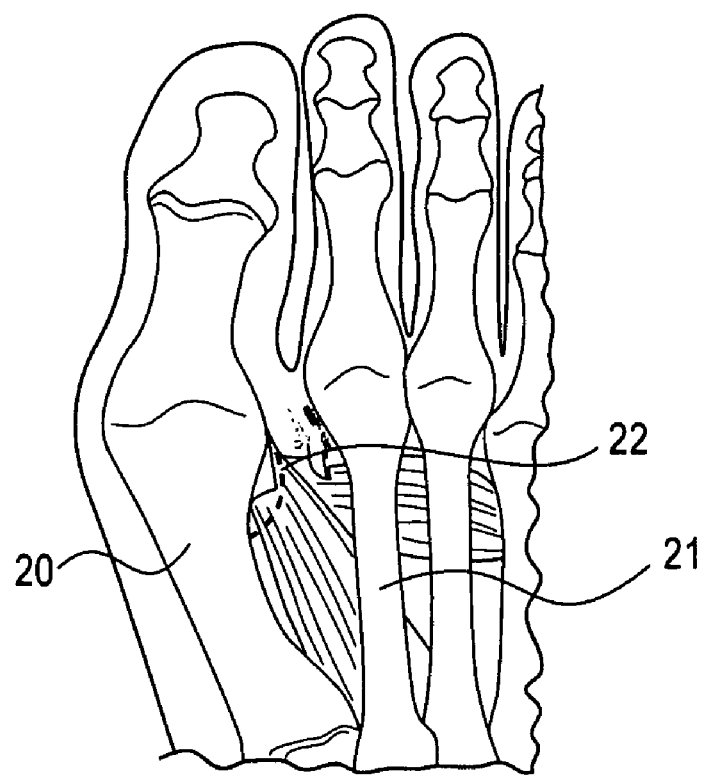
FIG. 5B illustrates a method of bunion repair using a distal approach, in accordance with a first embodiment of the present invention, and shows a first metatarsophalangeal joint at a preparation stage.
Figures 1, 5B:
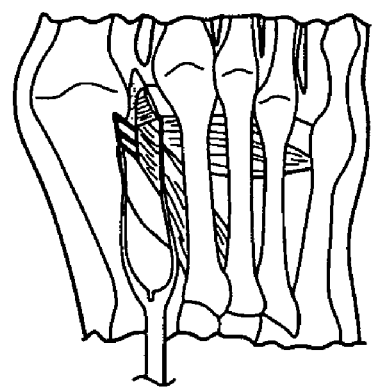

A patient's foot with a hallux valgus deformity that needs a bunion repair is shown in FIG. 5A. FIGS. 5B-5K show a bunion repair surgical technique using a distal approach for placement of the suture-button construct, in accordance with a first embodiment of the invention. First, the adductor tendon from the base of the proximal phalanx and fibular sesamoid is detached to realign the fibular sesamoid, as shown in FIG. 5B. The deep intermetatarsal ligament is then released to free any sesamoid adhesions to the intermetatarsal ligament. Following the release of the adductor tendon, release of the lateral capsule of the first metatarsophalangeal joint and release of the intermetatarsal ligament between the first metatarsal 20 and second metatarsal 21, the angular deformity of the hallux valgus is manually tested. For a distal approach, a first incision 22 is made between the first and second metatarsals 20, 21 to release the inner space.

Figure 5C:
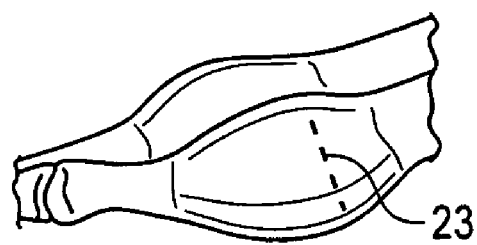
FIG. 5C illustrates the medial aspect of the first metatarsophalangeal joint of FIG. 5B at a stage subsequent to that shown in FIG. 5B and shows the entire medial eminence, in accordance with a first embodiment of the present invention.
Figures 1, 5C:
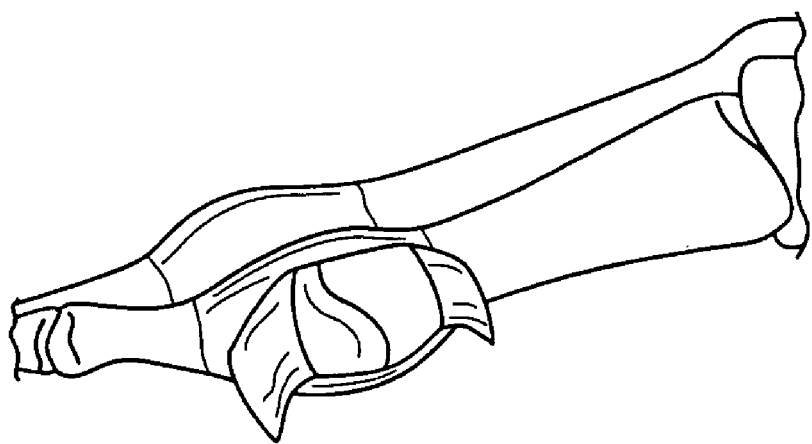
Figure 5D:
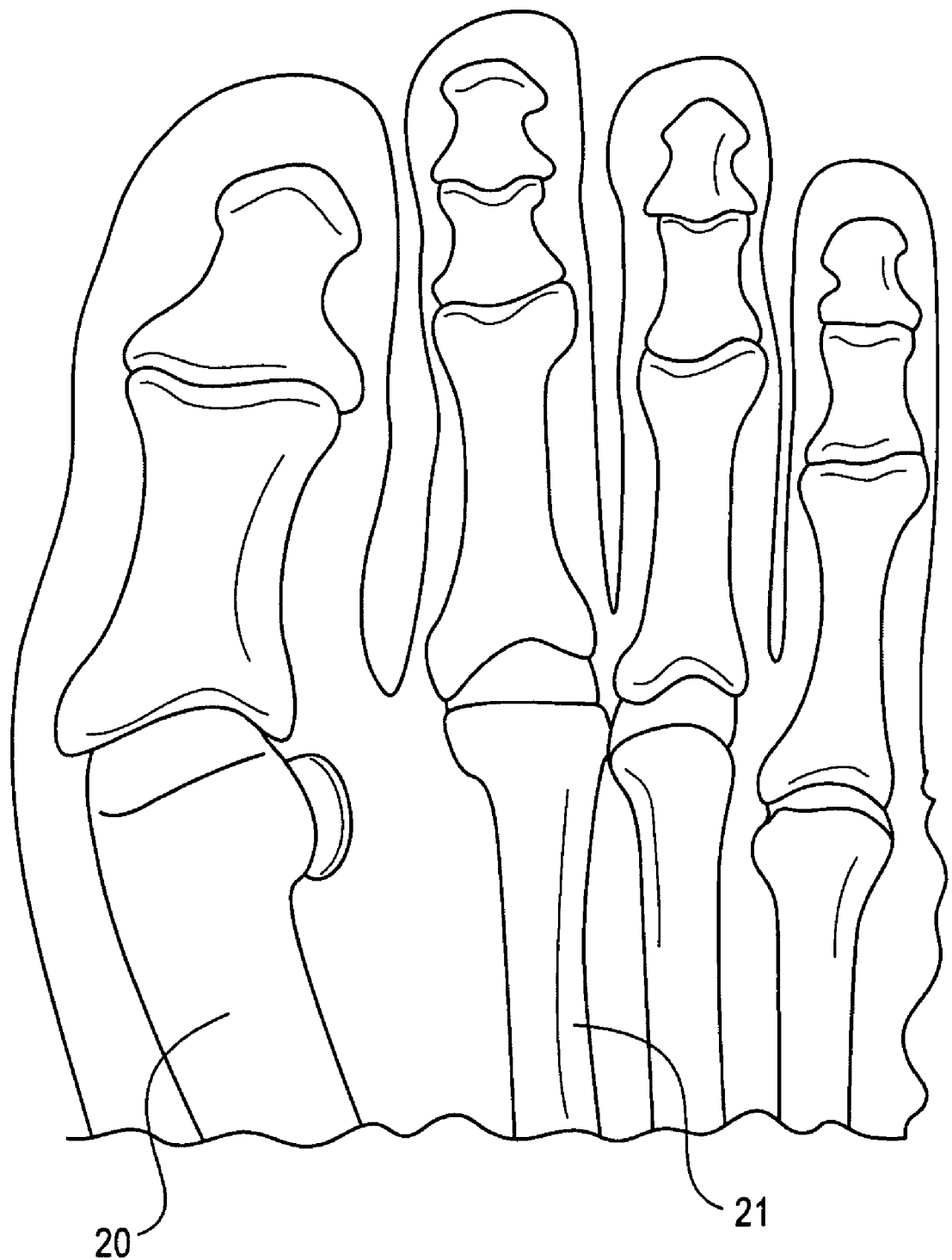
FIG. 5D illustrates the first metatarsophalangeal joint of FIG. 5B at a stage subsequent to that shown in FIG. 5C and shows removal of the medial eminence, in accordance with a first embodiment of the present invention.

Referring to FIGS. 5C-5D, a longitudinal incision 23, as shown in the insert of FIG. 5C, over the medial aspect of the first metatarsophalangeal joint is made to expose the entire medial eminence. The medial eminence preserving the sesamoid groove on the plantar aspect of the first metatarsal 20 is removed while avoiding excessive resection of the medial eminence.

Figure 5E:
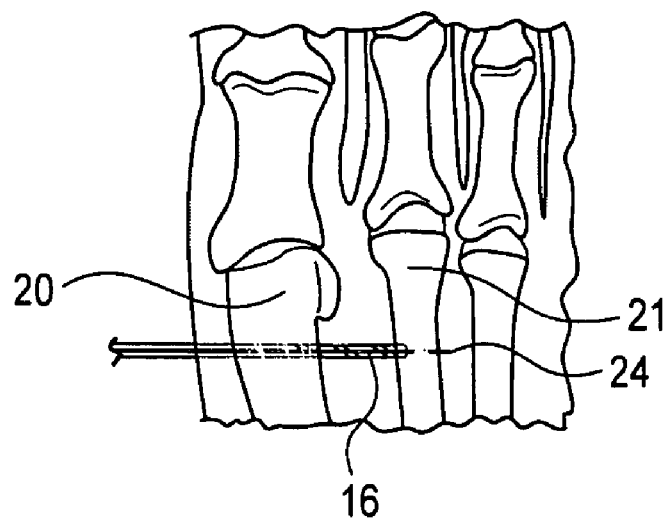
FIG. 5E illustrates the first metatarsophalangeal joint of FIG. 5B at a stage subsequent to that shown in FIG. 5D and shows a guidewire placed across the first and second metatarsals and a drill bit drilling a hole in the first and second metatarsals, in accordance with a first embodiment of the present invention.
Figures 1, 5E:
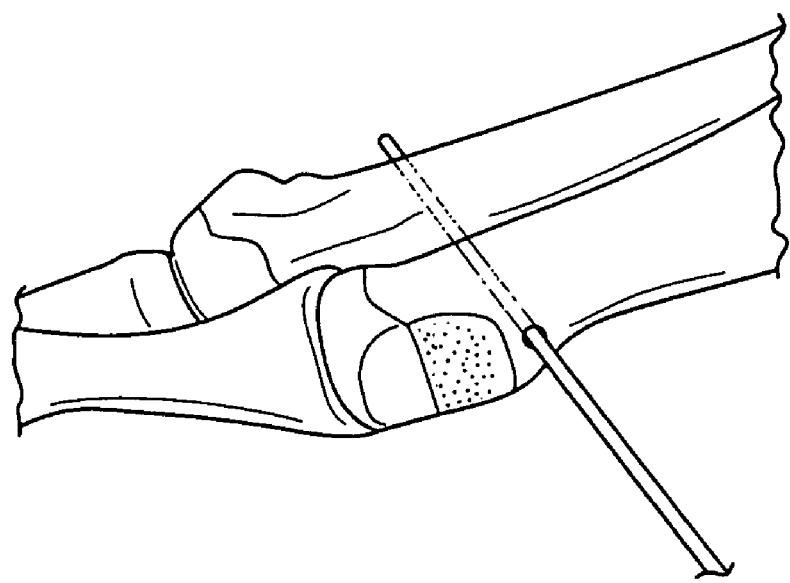

Referring to FIG. 5E, using a C-Arm for guidance, a guidewire 24, as shown in the insert, preferably about 1.2 mm, is inserted across the first metatarsal 20 and through the second metatarsal 21. A guidewire pilot hole is formed just proximal to the excised medial eminence at a slight plantar-to-dorsal angle to ensure accurate pin placement and penetration of the second metatarsal 21 at its midpoint. The entry point on the second metatarsal 21 should be about 2-5 mm proximal to the neck of the second metatarsal head. As shown in the insert, using a cannulated drill bit 16, preferably a 2.7 mm drill bit, a hole is drilled across a first metatarsal and through a second metatarsal for the placement of a suture-button construct. Proper placement of the cannulated drill bit 16 is confirmed with the C-Arm. Alternatively, a K-wire (Kirschner wire) may be used to drill the hole.

Figure 5F:
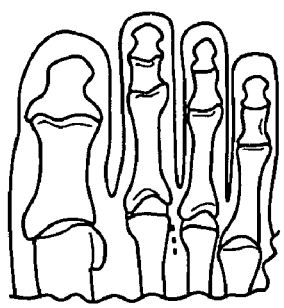
FIG. 5F illustrates the first metatarsophalangeal joint of FIG. 5B at a stage subsequent to that shown in FIG. 5E and shows a guide pin with pull-through suture strand being advanced in the hole drilled in the first and second metatarsals, in accordance with a first embodiment of the present invention.
Figures 1, 5F:
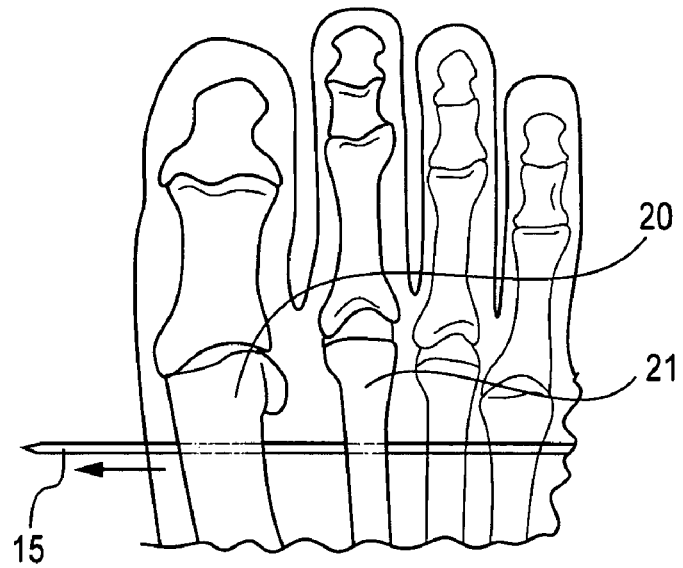
Figures 2, 5F:
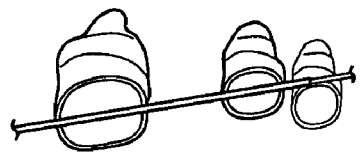

Referring to FIG. 5F, a pull-through needle 15, preferably a 1.2 mm guide pin, with a pull-through suture strand is passed through the hole at an angle lateral of the second metatarsal 21 to a medial of the first metatarsal 20 and stopped before a first button 12 (FIG. 5G) enters the drill hole.

Figure 5G:
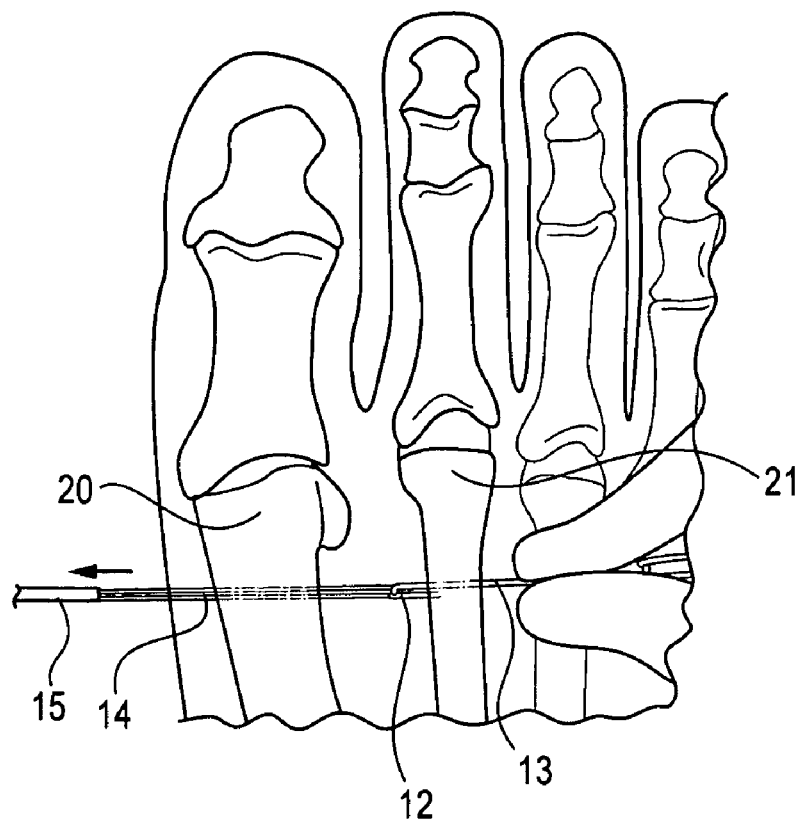
FIG. 5G illustrates the first metatarsophalangeal joint of FIG. 5B at a stage subsequent to that shown in FIG. 5F and shows the pull-through suture strand being pulled to advance a first button of the construct through the hole, in accordance with a first embodiment of the present invention.
Figures 1, 5G:
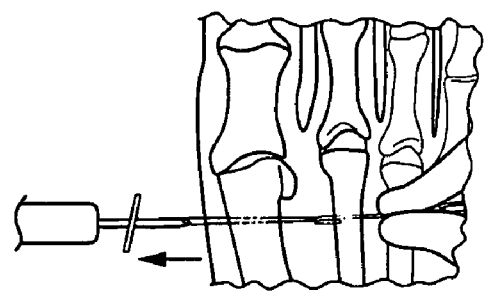

The pull-through suture strand 14 is pulled and a lateral tension is simultaneously applied on a first suture strand 13 such that the first button 12 of the construct lies sideways for passage through the hole, as shown in FIG. 5G. The pull-through suture strand 14 is now advanced while the pull-through needle 15 is pulled medially. Alternatively, the pull-through needle 15 can be removed, leaving just the pull-through suture strand 14. A straight suture, preferably Micro SutureLasso™, AR-8703 sold by Arthrex, Inc., can then be used to pass the pull-through suture strand 14 through the hole in the first and second metatarsals 20, 21.

Figure 5H:
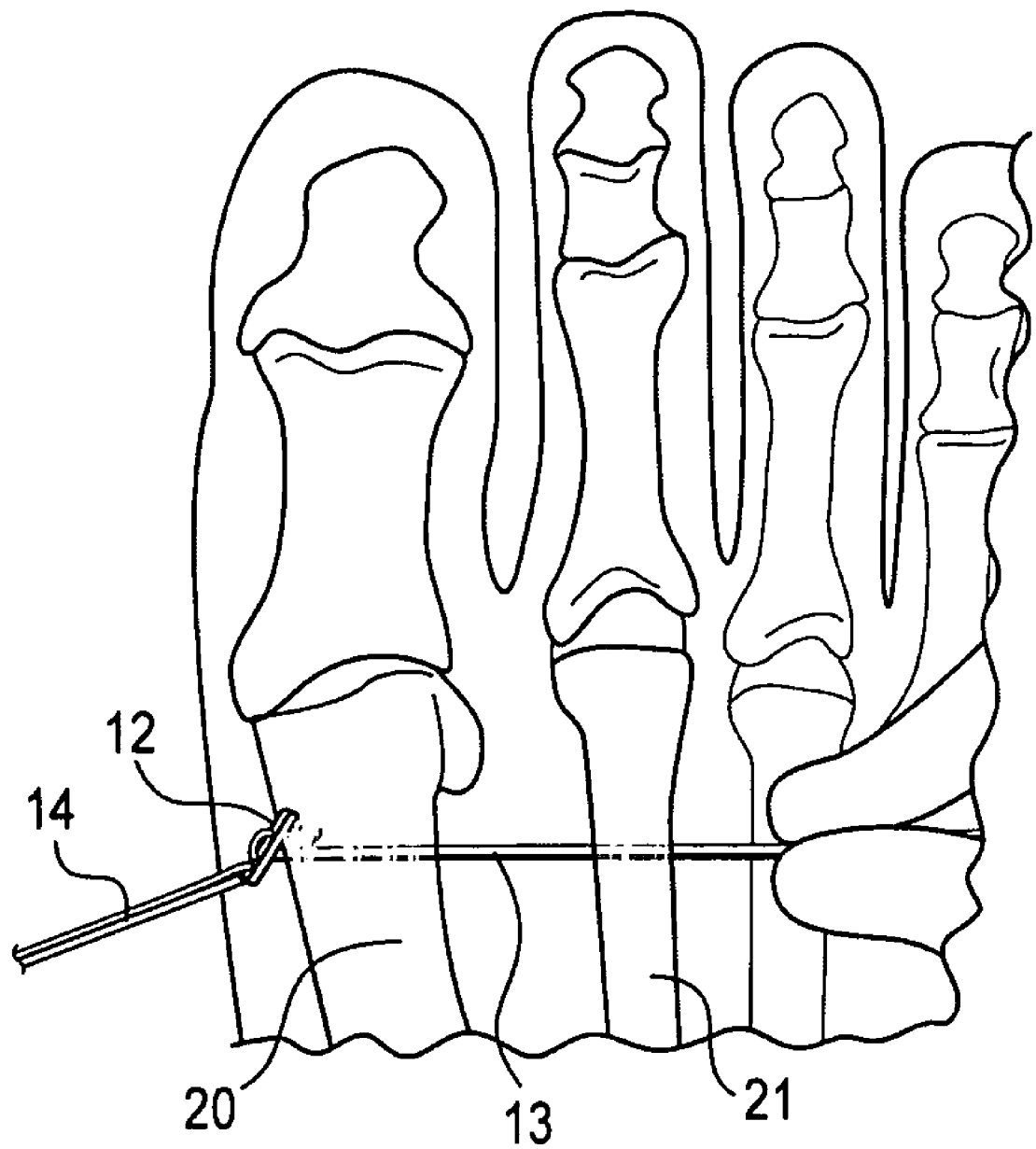
FIG. 5H illustrates the first metatarsophalangeal joint of FIG. 5B at a stage subsequent to that shown in FIG. 5G and shows the first button of the construct exiting the hole on the medial/lateral side of the first metatarsal cortex, in accordance with a first embodiment of the present invention.
Figure 5I:
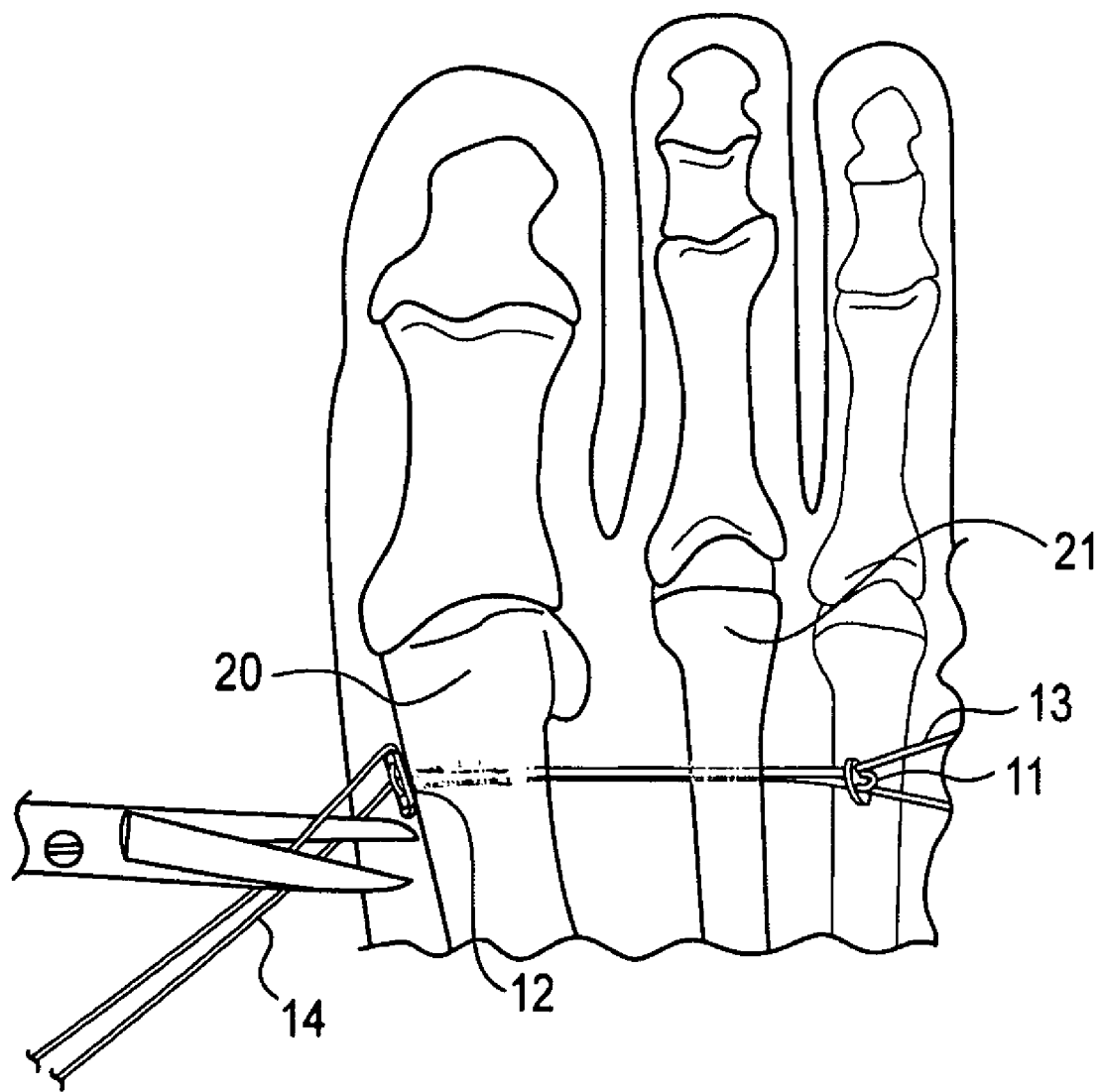
FIG. 5I illustrates the first metatarsophalangeal joint of FIG. 5B at a stage subsequent to that shown in FIG. 5H and shows the seating of the first button of the construct against the first metatarsal and the pulling of the free ends of the first suture strand of the construct, in accordance with a first embodiment of the present invention.

Referring to FIG. 5H, the first button 12 of the construct is then advanced through the hole until it exits the hole through the first metatarsal 20 on the medial side of the first metatarsal cortex. Once the first button 12 of the construct has exited the hole on the medial side of the first metatarsal 20 cortex, a lateral tension is applied on the first suture strand 13 to seat the first button 12 against the first metatarsal 20. The pull-through suture strand 14 is then cut and removed, as shown in FIG. 5I.

Figure 5J:
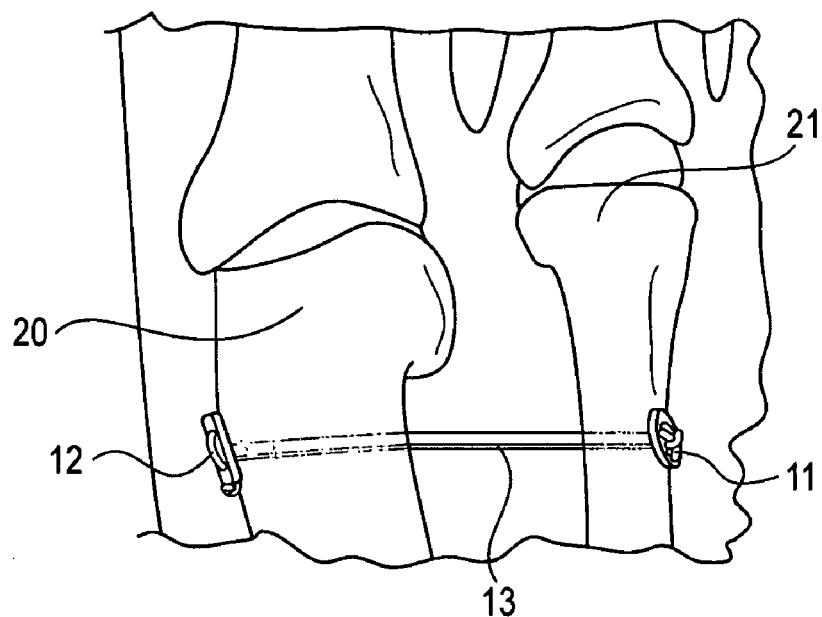
FIG. 5J illustrates the first metatarsophalangeal joint of FIG. 5B at a stage subsequent to that shown in FIG. 5I and shows the seating of two buttons of the construct, one each against the first and second metatarsals, in accordance with a first embodiment of the present invention.
Figures 1, 5J:
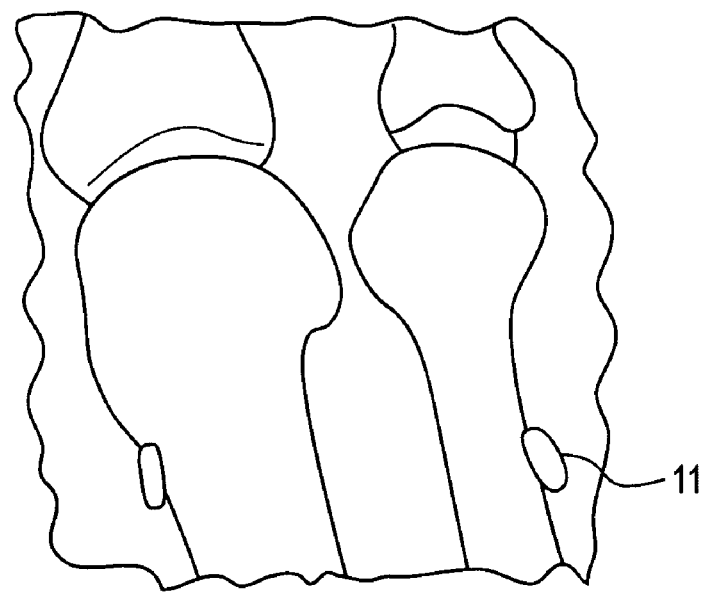
Figure 5K:
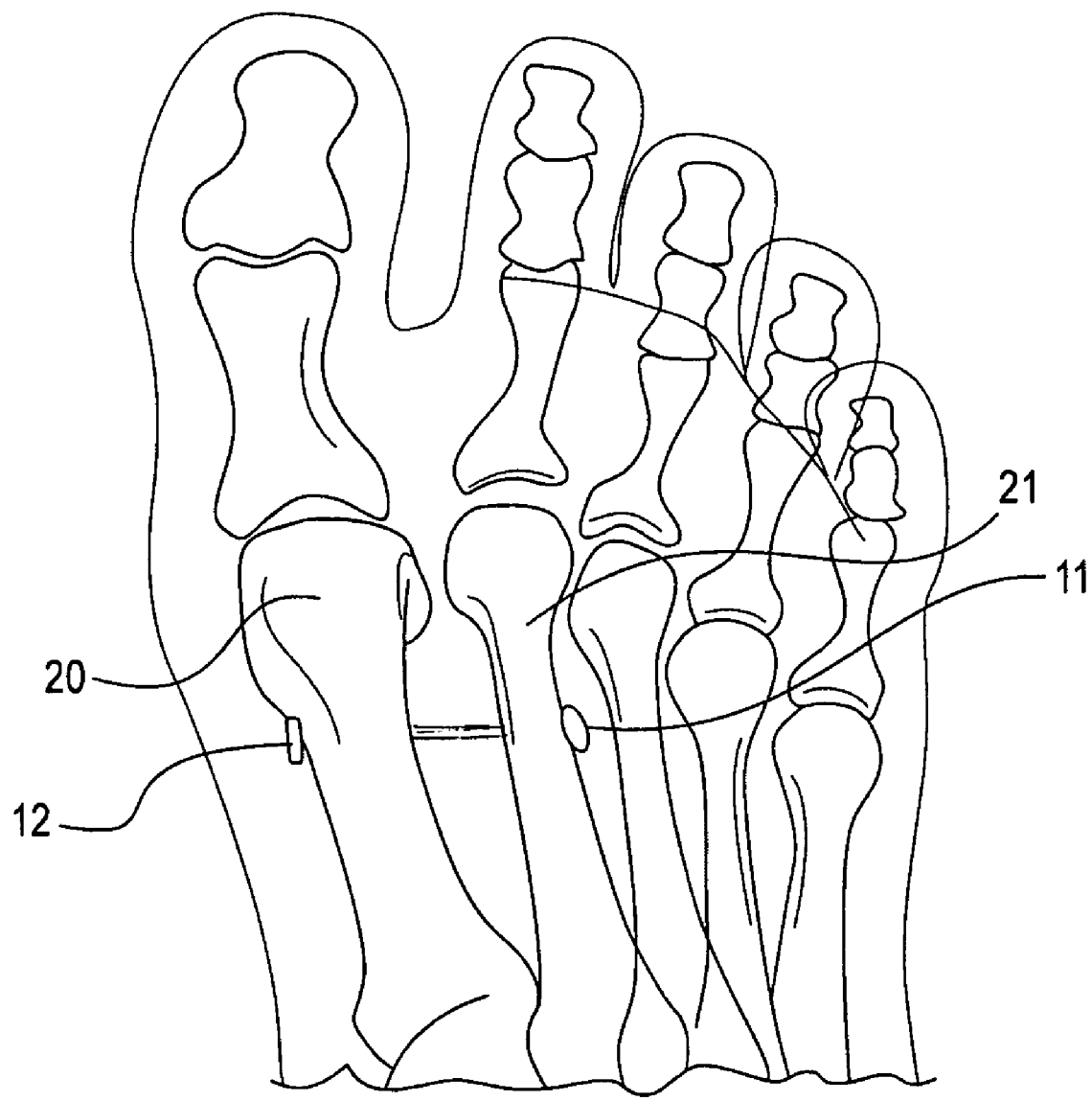
FIG. 5K shows a patient's foot subsequent to performing a bunion repair in accordance with a first embodiment of the present invention.

The surgeon may manually push the first metatarsal and the second metatarsal together to correct the intermetatarsal angular deformity. Once fluoroscopy confirms proper positioning, the free ends of a first suture strand 13 are pulled to advance the second button 11 of the construct to seat the second button 11 against the second metatarsal 21, as shown in FIG. 5J. The free ends of the first suture strand 13 are tied by making a surgeon's knot and two reverse half-hitches. Any remaining first suture strand 13 is removed by cutting and pulling them out of the first and second buttons 20, 21 of the construct. The patient's foot subsequent to performing the bunion repair using a distal placement surgical technique, in accordance with a first embodiment of the present invention, is shown in FIG. 5K.

Figure 5L:
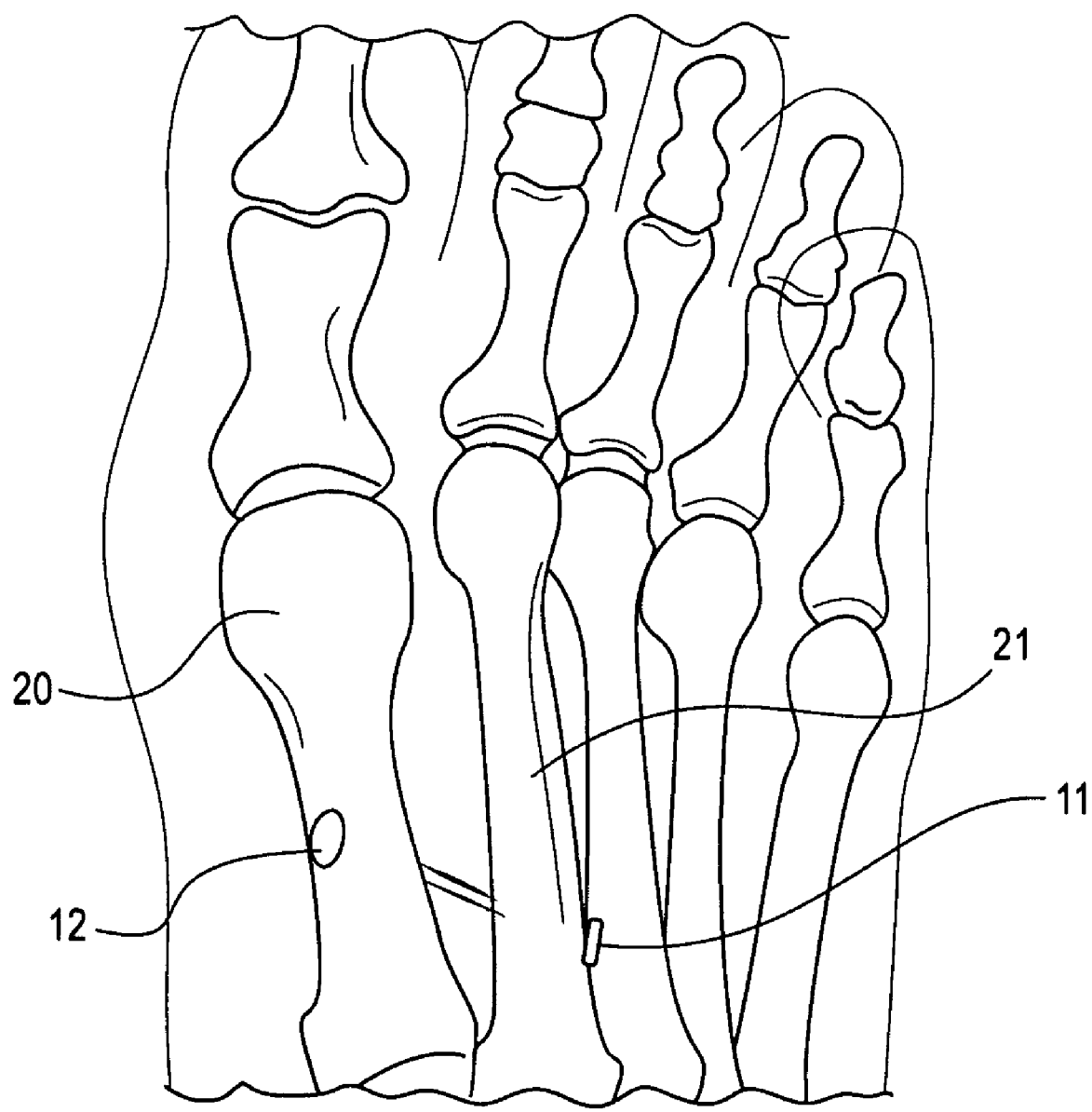
FIG. 5L shows two buttons, one each against the first and second metatarsals, placed using a proximal placement technique in accordance with a second embodiment of the present invention.

Referring to FIG. 5L, the surgical technique for repairing bunions using the suture-button construct, as described in the earlier paragraphs, may also be performed by inserting the cannulated guide wire by starting between about 2.5 cm and about 3.5 cm distal to metatarsal-cuneiform joint on the first metatarsal just below midline, drilling a hole using a cannulated drill bit into the superior second metatarsal metaphyseal bone, observing under the C-arm, performing the plantarflexion of the third metatarsal to allow passage of the guide pin, tightening the first button 12 over the first metatarsal 20 and the second button 11 over the second metatarsal 21 by pulling on the first suture strand, and securing the first suture strand by a knot.

The surgical method of the present invention can also optionally be performed in the opposite direction as that described above, such that the first button 12 ends up on the lateral side of the second metatarsal and the second button 11 ends up on the first metatarsal 20.

Figure 6:
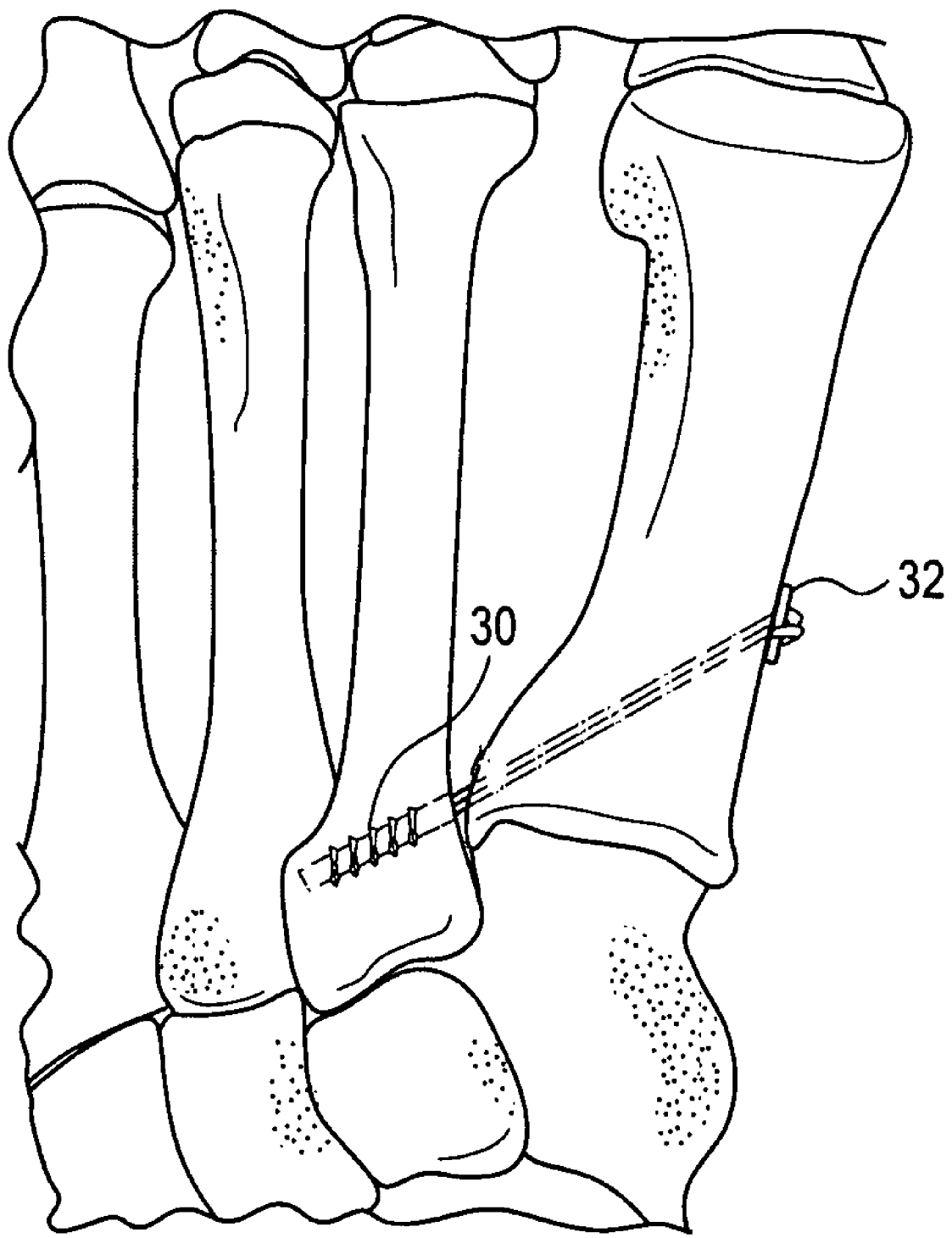
FIG. 6 shows an alternative suture anchor-button construct for use in the present invention, which has a fully threaded suture anchor at one end, and a round, cup-shaped button at the opposite end, the suture anchor and the button being connected by suture.

In yet another embodiment of the present invention, shown in FIG. 6, a suture anchor-button construct is used for bunion repair. The suture anchor-button construct comprises a fully threaded suture anchor 30 connected by suture extending therefrom to a round button 32, which is preferably a cup-shaped button. The suture anchor 30 is inserted through a preformed hole formed in the first metatarsal and into a smaller diameter preformed hole in the second metatarsal, which it is screwed into place. After the first metatarsal and the second metatarsal are pushed together to correct the intermetatarsal angular deformity, the button 32 is advanced upon against the medial surface of the first metatarsal, with the cup of the button in the hole, and secured in place by the tying the suture strands passing through the button.

Implant Removal

Routine removal of the suture-button construct is typically not required. If, for any reason, the buttons need to be removed, they can be performed simply by small incisions over the first and the second button, cutting the first suture strand as it loops through the buttons and removing both the first and second buttons and the first suture strand.

Post Operation

Following bunion repair using the suture-button construct of the present invention, the patient's foot is placed in a soft dressing and the patient is allowed to bear weight with a walking boot or a postoperative stiff sole shoe. The patient is recommended to change the dressing weekly until suture removal at week two or three. Most patients are allowed to wear a comfortable shoe with a wide toebox about 4-5 weeks subsequent to the bunion repair procedure as illustrated above.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed is:

1. A method of bunion repair comprising:
drilling a hole across a first metatarsal and through a second metatarsal;
passing a needle with a first suture strand of a suture-button construct through the hole;
pulling the first suture strand and simultaneously applying a lateral tension on a second suture strand of the suture-button construct such that a first button of the suture-button construct lies sideways, and advancing the first button through the hole until the first button exits the hole through a medial side of the first metatarsal cortex;
flipping the first button to engage the first button against the first metatarsal and applying a lateral tension on the second suture strand;
manually pushing the first metatarsal and the second metatarsal together to correct intermetatarsal angular deformity;
pulling free ends of the second suture strand of the suture-button construct to advance a second button of the suture-button construct and to engage the second button against the second metatarsal; and
securing the second button against the second metatarsal.

2. The method of claim 1, wherein the first button is oblong-shaped having at least two apertures, the at least two apertures being substantially triangular in shape.

3. The method of claim 1, wherein the second button is round-shaped having at least four apertures, the four apertures being substantially circular-shaped and centers of the at least four apertures being substantially equidistant from a center of the second button.

4. The method of claim 1, wherein the first and second suture strands are formed of a suture comprising a plurality of fibers of ultrahigh molecular weight polyethylene.

5. The method of claim 1, further comprising the initial step of making a longitudinal incision over a medial aspect of a first metatarsophalangeal joint to expose a medial eminence; and removing the medial eminence.

6. A method of bunion repair comprising:
drilling a hole across a first metatarsal and through a second metatarsal;
passing a needle with a first suture strand of a suture-button construct through the hole;
pulling the first suture strand and simultaneously applying a lateral tension on a second suture strand of the suture-button construct such that a first button of the suture-button construct lies sideways, and advancing the first button laterally through the hole until the first button exits the hole through a lateral side of the second metatarsal cortex;
flipping the first button to engage the first button against the lateral side of the second metatarsal and applying a lateral tension on the second suture strand;
manually pushing the first metatarsal and the second metatarsal together to correct intermetatarsal angular deformity;
pulling free ends of the second suture strand of the suture-button construct to advance a second button of the suture-button construct and to engage the second button against the medial side of the first metatarsal; and
securing the second button against the first metatarsal.

* * * * *